United States Patent [19]

Lott et al.

[11] Patent Number: 5,426,027

[45] Date of Patent: Jun. 20, 1995

[54] NUCLEIC ACID PROBES AND METHODS FOR DETECTING CANDIDA DNA CELLS IN BLOOD

[75] Inventors: Timothy J. Lott; Christine J. Morrison, both of Atlanta; Errol Reiss, Chamblee; Brent Lasker; Sandra Zakroff, both of Atlanta, all of Ga.

[73] Assignee: The Government of the United States of America as represented by the Secretary, Washington, D.C.

[21] Appl. No.: 65,845

[22] Filed: May 20, 1993

[51] Int. Cl.$^6$ .................... C12Q 1/68; C12P 19/34; C07H 21/04

[52] U.S. Cl. ...................... 435/6; 435/91.2; 536/24.32; 536/24.33

[58] Field of Search ............... 435/6, 91.2; 536/24.32, 536/24.33; 935/17, 78

[56] References Cited

FOREIGN PATENT DOCUMENTS

0422969A2 8/1990 European Pat. Off. ........ C12Q 1/68

OTHER PUBLICATIONS

Huffman, et al. Authentication of ATCC Strains in the Saccharomyces—cerevisiae complex . . . (1993) Exp. Mycol. 16:316–319. (Abstract).
Zakroff et al. Abstract No. 100930 Amer. Soc. for Microbiol. Gen. Meeting, Atlanta, Ga. May 1993.
Lott et al. Abstract Amer. Soc. for Microbiol. Gen. Meeting, Atlanta, Ga. May 1993.
Niesters et al. *J. Clin. Microbiol.* 31(4):904–910, Apr. 1993.
Hopfer et al. *J. of Med. and Vet.* 31:65–75, 1993.
Kan/Bennett Abstract 1627, Interscience Conf. on Anti-Microbial Agents Chemotherapy, Oct. 1992.
Rand/Houck Abstract 1628, Interscience Conf. on Anti-Microbial Agents Chemotherapy, Oct. 1992.
Crampin, A. C. Abstract, *J. Med. Microbiol.* 37 (supp.1) Abst. No. 283, Jul. 1992.
Lehmann et al. Abstract F-16, Gen. Meet. Am. Soc. Microiol. New Orleand, La., May 1992.
Miyakawa et al. *J. of Clin. Microbiol.* 30(4):894–900, Apr. 1992.
Oren et al. Abstract D-46 Gen. Meeting Am. soc. for Microbiol., Dallas, Tex., May 1991.
Lott/Kuykendall Abstract F-78 Gen. Meeting Am. soc. for Microbiol., Dallas, Tex., May 1991.
Barns et al. *J. of Bacteriol.* 173(7-8):2147–2731, 1991.
Jones, J. *J. Clin. Microbiol.* Rev. 3:32–45, 1990.
Buchman et al. *Surgery* 108:338–347, 1990.
White et al. *PCR Protocols:A Guide to Methods and Applications* Innis et al. Eds. Academic Press, Inc. pp. 315–322, 1990.
Hendricks et al. *System. Appl. Microbiol.* 12:223–229, 1989.
Yue et al. Abstract, *Clinical Research* 37(2):446A, 1989.

Primary Examiner—Margaret Parr
Assistant Examiner—David Schreiber
Attorney, Agent, or Firm—Needle & Rosenberg

[57] ABSTRACT

Provided is an isolated double-stranded nucleic acid consisting essentially of the nucleotide sequence defined in the Sequence Listing by SEQ ID NO:5. This is the *C. albicans* ITS2 sequence and includes a nucleic acid comprising a nucleotide sequence that is specific for *Candida albicans*. Further examples of an isolated double stranded nucleic acid of the present invention consist essentially of the nucleotide sequences defined in the Sequence Listing by SEQ ID NOs:6–9. These are the ITS2 sequences for *C. parapsilosis, C. tropicalis, C. glabrata* and *C. krusei*. A method of diagnosing systemic candidiasis in a subject is also provided. The method comprises the steps of: (a) collecting blood from the subject into tubes containing detergent, polypropylene glycol, sodium polyanetholesulfonate, and sodium ethylene diamine ® tetraacetic acid; (b) lysing Candida cells using ZYMOLYASE ®-100T with agitation; (c) extracting and precipitating the DNA from the lysed cells; (d) amplifying the precipitated DNA using universal fungal primer pairs derived from the internal transcribed spacer regions of the Candida ribosomal DNA; and (e) detecting amplified DNA from Candida by hybridizing the amplified DNA with a probe that selectively hybridizes with Candida DNA, the presence of amplified DNA indicating systemic candidiasis.

10 Claims, No Drawings

NUCLEIC ACID PROBES AND METHODS FOR DETECTING CANDIDA DNA CELLS IN BLOOD

BACKGROUND OF THE INVENTION

*Candida albicans* is a commensal of the gastrointestinal tract. *C. albicans,* and to a lesser extent several other related species, are of increasing importance as opportunistic pathogens in immunocompromised hosts. A dimorphic, diploid yeast with no known sexual cycle, *C. albicans* is an endogenous organism that can be isolated from skin and mucosal tissues of persons whose immune systems are intact. However, perturbations of the immune or endocrine systems can create opportunities for Candida species to convert from a commensal state to invade tissues either locally or systemically. An example of this opportunism is the oral-esophageal or vaginal candidiasis that is encountered in association with HIV infection. In *C. albicans,* the nuclear rDNA genes encoding the 5S, 18S, 5.8S, and 28S rRNAs are found as 50–100 copy tandem repeats of approximately 10 kb unit length on chromosome seven (Magee et al., 1987, Thrash-Bingham and Gorman, 1992). The 5S rDNA gene (121 bp) is flanked by two nontranscribed regions located between the small and large subunits, and collectively termed the intergenic spacer (IGS). Ribosomal 5.8S sequences have been compiled from a variety of eukaryotes (Dams et al., 1988). In addition, sequence analysis of the 5.8/28S internally transcribed spacer (ITS) region has shown strain variation within at least one fungal species (O'Donnell, 1992), while other species have demonstrated complete conservation (Mitchell et al., 1992). Strain-specific restriction polymorphisms (RFLPs) have previously been observed in the IGS region for *C. albicans* (Magee et al., 1987).

An opportunistic fungus, *C. albicans* also causes systemic disease in severely immunocompromised hosts. It is the most causative species of disseminated candidiasis followed by *C. tropicalis, C. parapsilosis,* and *C. glabrata* (Odds, 1988). Dissemination occurs when Candida is spread via the bloodstream or by invasion of mucosal surfaces to internal organs (Odds, 1988). High-risk patient populations include individuals with malignancy or neutropenia, those receiving chemotherapy and/or multiple antibiotics, and those with indwelling catheters or low birth weight infants (Armstrong, 1989).

Diagnosis of systemic candidiasis is complicated by the absence of clinically distinguishing signs, frequently negative blood cultures, and the absence of a reliable serological test to detect infection. Currently, disseminated candidiasis is often diagnosed by a minimum of at least two positive blood cultures (Odds, 1988). However, blood culture alone is clearly not sufficient for the diagnosis of disseminated candidiasis since as many as 50% of disseminated candidiasis cases are diagnosed at autopsy (Telenti, et al. 1989). The nephrotoxicity of amphotericin B, the drug of choice for immunocompromised patients with disseminated disease, precludes its use for prophylaxis.

These facts, in conjunction with the difficulty of reliably culturing candida from the blood and the lack of a sensitive and specific serological test to detect disease, underscore the need to develop alternative diagnostic approaches.

Technology has been developed for the detection of bacterial and viral DNA from the bloodstream of infected patients through the use of the polymerase chain reaction (PCR). The PCR amplifies genomic DNA geometrically so that it may be detected by agarose gel electrophoresis, Southern blotting, or dot blot hybridization (Miyakawa et al. 1992, Kafatos et al. 1979, Lasker et al. 1992).

PCR-based diagnostic methods may provide increased sensitivity relative to blood culture techniques since viable organisms are not required for amplification or detection. There has only been one report to date describing the detection of *C. albicans* cells in infected patient blood through the use of PCR-amplified DNA (Buckman et al. 1990). Buchman et al. lysed *C. albicans* cells with zymolyase and proteinase K and extracted the DNA with phenol and chloroform. The limit of sensitivity by this method was 120 cells per ml of whole blood. As described, this method was time consuming, labor-intensive, repeatedly used toxic chemicals (phenol and chloroform), and has not been shown to be readily reproducible. In addition, a single copy gene, the cytochrome P-450 gene, was the target for DNA amplification, thus making the method much less sensitive. Miyakawa et al. described improved sensitivity by use of Southern blot hybridization for the detection of PCR products from Candida DNA (Miyakawa et al. 1991). The limit of sensitivity by Southern blot in their study was 10 cells per ml of urine and did not address detection in blood.

The ability to detect Candida in blood is crucial for the rapid and accurate diagnosis of systemic candidiasis, because detection from urine or mucosal secretions can be confused with the normal commensal status of the organism or a localized non-disseminated infections. The present invention provides a rapid method for the isolation, release, purification and amplification of *C. albicans* DNA from blood and other body fluids of infected patients. This method minimizes the use of phenol and chloroform and uses universal fungal primers to the multi-copy ITS region of rDNA, to enhance detection of Candida DNA. The invention provides a rapid approach to species identification through the use of non-conserved regions of the ITS2 flanked by highly conserved, functional domains.

SUMMARY OF THE INVENTION

The present invention provides an isolated double-stranded nucleic acid consisting essentially of the nucleotide sequence defined in the Sequence Listing by SEQ ID NO:5. This is the *C. albicans* ITS2 sequence and includes a nucleic acid comprising a nucleotide sequence that is specific for *C. albicans*. Further examples of an isolated double stranded nucleic acid of the present invention consist essentially of the nucleotide sequences defined in the Sequence Listing by SEQ ID NOs:6-9. These are the ITS2 sequences for *C. parapsilosis, C. tropicalis, C. glabrata* and *C. krusei*. These nucleic acids can include a nucleotide sequence that is specific for the respective organism.

An isolated nucleic acid that specifically hybridizes with or selectively amplifies a nucleic acid of the invention or fragments thereof is also contemplated. An isolated nucleic acid complementary to the above nucleic acid is also provided.

A method of diagnosing systemic candidiasis in a subject is also provided. The method comprises the steps of: (a) collecting blood from the subject into tubes containing detergent, polypropylene glycol, sodium polyanetholesulfonate, and sodium ethylene diamine tetraacetic acid; (b) lysing Candida cells using ZYMOLASE®-100T with agitation; (c) extracting and precipitating the DNA from the lysed cells; (d) amplifying the precipitated DNA using universal fungal primer pairs derived from the internal transcribed spacer regions of the Candida ribosomal DNA; and (e) detecting amplified DNA from Candida by hybridizing the amplified DNA with a probe that selectively hybridizes with Candida DNA, the presence of amplified DNA indicating systemic candidiasis.

DETAILED DESCRIPTION OF THE INVENTION

The present invention provides an isolated double-stranded nucleic acid consisting essentially of the nucleotide sequence defined in the Sequence Listing by SEQ ID NO:5. This includes the C. albicans ITS2 sequence. "isolated" is meant separated from other nucleic acids found in the naturally occurring organism. The nucleic acid comprises a nucleotide sequence that is specific for C. albicans. By "specific" is meant a sequence which does not hybridize with other nucleic acids to prevent determination of an adequate positive hybridization with nucleic acids from C. albicans. Probes which "specifically hybridize" with the double-stranded nucleic acid are hybridizing with one of the two strands when in single stranded form.

A further example of an isolated double stranded nucleic acid of the present invention consists essentially of the nucleotide sequence defined in the Sequence Listing by SEQ ID NO:6. This includes the ITS2 sequence for C. parapsilosis. This nucleic acid comprises a nucleotide sequence that is specific for C. parapsilosis.

Another example of the isolated double stranded nucleic acid of the invention consists essentially of the nucleotide sequence defined in the Sequence Listing by SEQ ID NO:7. This includes the C. tropicalis ITS2 sequence. This nucleic acid comprises a nucleotide sequence that is specific for C. tropicalis.

A still further example of the isolated double stranded nucleic acid of the invention consists essentially of the nucleotide sequence defined in the Sequence Listing by SEQ ID NO:8. This includes the C. glabrata ITS2 sequence. This nucleic acid comprises a nucleotide sequence that is specific for C. glabrata.

Another example of the isolated double stranded nucleic acid of the invention consists essentially of the nucleotide sequence defined in the Sequence Listing by SEQ ID NO:9. This includes the C. krusei ITS2 sequence. This nucleic acid comprises a nucleotide sequence that is specific for C. krusei.

An isolated nucleic acid that specifically hybridizes with or selectively amplifies a nucleic acid of the invention or fragments thereof is also contemplated. An isolated nucleic acid complementary to the above nucleic acid is also provided. The sequences can be selected based on the nucleotide sequence and the utility of the particular sequence. More specifically the invention provides isolated nucleic acids that specifically hybridize with the nucleic acids consisting essentially of the nucleotide sequences defined in the Sequence Listing by SEQ ID NOs:5-9.

The term "consisting essentially of" as used herein includes modifications to the nucleic acids of the invention as long as the specificity (genus or species) of the nucleic acids is maintained. Likewise, fragments used as primers or probes can have substitutions so long as enough complementary bases exist for specific hybridization (Kunkel et al. *Methods Enzymol.* 1987:154:367, 1987).

The nucleic acid can have homology with nucleotide sequences present in more than one Candida species. Such a nucleic acid sequence shared with other Candida species can be used, for example, as a primer to simultaneously amplify nucleic acids from more than one Candida species. The amplified nucleic acids can then be detected using the specific nucleic acids described herein to permit either genus specific or species specific diagnosis. Thus, the specific nucleic acid can be specific for the genus Candida and can be used to detect any candidiasis in methods such as polymerase chain reaction, ligase chain reaction and hybridization.

A method of diagnosing systemic candidiasis in a subject is also provided. The method comprises the steps of: (a) collecting blood from the subject into tubes containing detergent, polypropylene glycol, sodium polyanetholesulfonate, and disodium ethylene diamine tetraacetic acid ((Na)$_2$EDTA); (b) lysing candida cells using ZYMOLASE®-100T with agitation; (c) extracting and precipitating the DNA from the lysed cells; (d) amplifying the precipitated DNA using universal fungal primer pairs derived from the internal transcribed spacer regions of the Candida ribosomal DNA; and (e) detecting amplified DNA from Candida by hybridizing the amplified DNA with a probe that selectively hybridizes with Candida DNA, the presence of amplified DNA indicating systemic candidiasis.

In the method, the lysis step can use the lysis buffer from the ISOQUICK® kit in addition to ZYMOLASE®-100T. The agitation step can be by rocking at about 16 cycles per minute. The extracting step can use the extraction matrix in the ISOQUICK® kit. In the amplification step of the above method, one of the primers of the primer pair is derived from the internal transcribed spacer 1 (ITS1) and the other primer of the primer pair is derived from the internal transcribed spacer 2 (ITS2). Alternatively, one of the primers of the primer pair is derived from the internal transcribed spacer 3 (ITS3) and the other primer of the primer pair is derived from the internal transcribed spacer 4 (ITS4). The detecting step hybridization can be by dot blot hybridization using a genus or species specific Candida probe.

In the method of detecting systemic candidiasis, the DNA that is amplified can be from C. albicans and the probe can specifically hybridize with a specific nucleotide sequence of the nucleic acid of SEQ ID NO:5 as described in Example 2. By using the other specific nucleic acids as provided herein, the method of Example 2 can be used to detect any of the other Candida species as taught herein. If the DNA that is amplified is from C. parapsilosis, the probe specifically hybridizes with a specific nucleotide sequence of the nucleic acid of SEQ ID NO:6. If the DNA that is amplified is from C. tropicalis, the probe specifically hybridizes with a specific nucleotide sequence of the nucleic acid of SEQ ID NO:7. If the DNA that is amplified is from C. glabrata, the probe specifically hybridizes with a specific nucleotide sequence of the nucleic acid of SEQ ID NO:8. If the DNA that is amplified is from C. krusei, the probe specifically hybridizes with a specific nucleotide sequence of the nucleic acid of SEQ ID NO:9. A nucleic acid having homology with more than one Candida species can also be used as a probe that specifically hybridizes with Candida DNA to detect systemic candidiasis.

Additionally, it is contemplated that the nucleic acids (e.g., probes and primers) can be attached to or labeled with (covalently or non-covalently) a detectable moiety. The probes may be suitably labeled using, for example, a radio label, enzyme label, fluorescent label, biotin-avidin label and the like for subsequent visualization in the example of the dot blot hybridization procedure taught in Example 2. An example of such a labeled nucleic acid is the digoxigenin-UTP labelled probe provided in Example 2, although others can be readily generated using standard methods (See, e.g., Sambrook et al., 1989). The nucleic acids specific for a given Candida species can each be labeled with a distinct detectable moiety, such that species specific probes for several species can be used with the same sample of amplified DNA to permit species specific diagnosis. The distinct label for each species specific probe can be detected in the sample if DNA from the particular species is present in the subject.

The detection of fungal DNA as described herein can also be performed using a ligase chain reaction (LCR). Essentially, this reaction, known to those of skill in the art, involves the use of, for each region to be detected, two primers that hybridize to the same strand of the target DNA, either abutting each other or with one or two nucleotides between the two primer sequences (i.e., "immediately 5'" or "immediately 3'" to the junction). The ligase reaction is performed, and the products are electrophoresed through a gel that can detect very small fragments, such as an SDS-polyacrylamide gel. A positive result is one in which a product equal in size to the sum of the two primers is produced, as this indicates the presence of all of the target DNA region. It is preferable that three reactions be run in three separate tubes, targeted at detecting (1) the first junction, (2) the second junction and (3) an internal sequence as a positive LCR control. If one wants to electrophorese all LCR products together through the gel, primers must be carefully chosen such that their individual sizes can be distinguished from the predicted size of any LCR products. Alternatively, the product of each reaction can be electrophoresed separately. Primers are preferably exactly homologous to the target region and of a size between approximately 20–40 nucleotides.

The following examples are intended to illustrate, but not limit, the invention. While they are typical of those that might be used, other procedures known to those skilled in the art may be alternatively employed.

EXAMPLES

Example 1

Nucleotide Sequence Analysis of the ITS2 Region of *Candida albicans* and Related Species.

Yeast strains and maintenance

All Candida isolates have been previously characterized by assimilation (API) profiles and morphology (Van der Walt and Yarrow, 1984). In addition, all *C. albicans* and *C. parapsilosis* isolates have previously been electrophoretically karyotyped and are known to represent distinct, non-related strains (Lasker et al., 1989). All isolates were grown and maintained on yeast-peptone-dextrose (YPD) medium (Guthrie and Fink, 1991). For DNA extractions, 10 ml of overnight cultures grown on YPD at 37° C. were washed twice in 1×TE buffer and the DNA extracted by standard procedures (Sambrook et al., 1989). Prior to PCR amplifications, DNA was digested with EcoRI restriction endonuclease (New England Biolabs), electrophoresed on 1.0% agarose gels, and stained with ethidium bromide (EtBr) to verify concentration and purity.

PCR amplification and DNA sequencing

Taq polymerase, buffers, and conditions for PCR were those supplied by the vendor (Perkin-Elmer/Cetus), using 100 ng genomic DNA per reaction. For primary amplifications, 35 cycles of 95° C., 55° C., and 72° C. at one min. intervals were followed by a five min. final extension at 72° C. The following "universal" ITS primers were used, for which calculated Tm's have previously been reported (White et al., 1990):

| ITS1 | 5' TCC GTA GGT GAA CCT GCG G 3' | (SEQ ID NO: 1) |
| ITS3 | 5' GCA TCG ATG AAG AAC GCA GC 3' | (SEQ ID NO: 2) |
| ITS4 | 5' TCC TCC GCT TAT TGA TAT GC 3' | (SEQ ID NO: 3) |

Primer ITS1 is to a conserved 3' domain in the 18S nuclear subunit. Primer ITS3 is approximately 25 bp from the end of the 5.8S subunit, and ITS4 is a reverse primer to a conserved region of the nuclear large rDNA. In addition, a -21M13 forward primer sequence (Messing et al. 1981) was added at the 5' end to primers ITS1 and ITS4 for sequencing in the forward and reverse directions, respectively, and consisted of the sequence: 5' GTAAAA CGA CGG CCA G 3' (SEQ ID NO:10) where the terminal 5' T of ITS1 and ITS4 made 17 bp of the 18 bp annealing sequence. From preliminary experiments it was determined that the addition of this sequence did not alter the nature of the derived PCR product. The aqueous phase of the primary PCR reaction was ethanol-precipitated, dried, and resuspended in 8 μl TE buffer. The entire amount was loaded into single wells of a 1.5% agarose, 1.0% NuSieve agarose gel (Lehmann et al. 1992), electrophoresed at 110 V., and stained with EtBr. Single, intensely staining bands of the appropriate size were excised and the DNA was extracted in Spin-X cellulose acetate columns (Costar, Inc.) for 30 min. at 40° C., 13000×g. The DNA was then ethanol- precipitated, washed twice in 70% EtOH, dried briefly, and resuspended in H2O for sequencing. Automated DNA sequencing (Smith et al. 1986), was performed using the Applied Biosystems Catalyst 800 workstation, with the "Prism" dye-primer dideoxy-sequencing reactions (Sanger et al. 1977), using conditions supplied by the vendor (Applied Biosystems). The precipitated DNA was dried and resuspended in 6 μl of formamide/50 mM EDTA (5:1), denatured for 2 min. at 90° C., and loaded on an Applied Biosystems model 373A DNA sequencer. All DNAs were sequenced in both forward and reverse orientations, and multiple runs were performed for all species and most strains within a given species.

5.8s rDNA 5.8S sequence alignments were performed both manually and with the "pileup" program from the University of Wisconsin Genetics Computer Group (GCG) package (Devereux et al., 1984). ITS alignments were performed in all possible pairwise combinations using the Needleman and Wunsch algorithm as implemented by GCG (Needleman and Wunsch 1970). DNA parsimony and bootstrap analysis was performed using the "Phylip" programs of Felsenstein (Felsenstein 1982), implemented on a micro-vax (Digital Equip. Corp.) cluster. Dendrograms were constructed using the global option and using a variety of different species as the outgroup (Felsenstein 1985). Other 5.8S sequences were: *Neurospora crassa, Shizosaccharomyces pombe, Saccharomyces cerevisia, Pneumocystis carinii, Fusarium sambucium, Epichloe typhina, Cephalosporium remonium, Lentinula edodes.*

For *C. albicans* and *C. parapsilosis,* where multiple strains were analyzed, there was complete nucleotide conservation within the entire 159 bp 5.8S region. The greatest degree of diversity for the species used in this study was found in the two relatively unconserved regions between bp 79–85 and bp 118–136. The overall average degree of diversity between the Candida species was approximately three percent. The minimum degree of diversity was found between *C. tropicalis* and *C. parapsilosis,* with a single C-A transversion at bp 62. Interestingly, both *C. albicans* and *C. krusei* contained A-G transitions in the termination consensus TCATTT.

A phylogenetic analysis was performed with all known fungal 5.8S sequences using strict parsimony as implemented by Felsenstein and statistical bootstrap analysis (Felsenstein 1982; 1985). *P. carinii* was used as the outgroup considering previous findings based on 18S analysis using a larger database of eukaryotic organisms (Edman et al. 1988). There were a total of 47 informative sites for the number of fungal sequences compiled, including 4 single base pair gaps. Re-analysis of the data set without gaps did not significantly alter the tree topology. The cumulative number of positive selections out of 100 total iterations is given for each branch point. The derived tree does not differ significantly from previous research using a weighted difference algorithm for 18S sequences, and supports the view that these species are related such that *C. albicans, C. parapsilosis* and *C. tropicalis* are more closely aligned than *C. krusei* within a clade. Likewise, *C. glabrata* appears more distantly related and can equally be placed at a number of positions within the larger branch of yeast-like fungi. It is generally accepted that values of 70 or greater out of 100 randomly tested samples will represent similar trees to a significant degree of probability.

ITS2 rDNA

The sequences of the ITS2 regions for *C. albicans, C. parapsilosis, C. tropicallis, C. labrata* and *C. krusei* are shown in the Sequence Listing as SEQ ID NOs:5–9.

A total of ten *C. albicans* isolates, representing typical and morphologically (or physiologically) atypical strains, were found to be identical at the nucleotide level within the ITS region. Similarly, five strains of *C. parapsilosis,* displaying a wide range of electrophoretic karyotypes and randomly amplified polymorphisms (RAPD), were also identical to the type strain for the species. The entire length of the ITS region was found to be species specific.

Similar to the results of the 5.8S alignments, we found that *C. albicans, C. parapsilosis,* and *C. tropicalis* were also most homologous in this ITS region. This homology extended for the first 57 bp 5' immediately adjacent to the termination of the 5.8S sequence. In contrast, the 3' region displayed little homology. For *C. krusei* and *C. glabrata* there was no apparent homology either to each other or to members of the *C. albicans* group over this entire ITS region. Sequences were aligned in all possible pairwise combinations (Needleman and Wunsch 1970), and the average degree of similarity was found to be approximately 40 percent.

Analysis of the ITS2 region has revealed that *C. albicans,* and possibly other closely related species, displays no interstrain variation. In this respect this species resembles the opportunistic fungus *Cryptococcus neoformans,* and is unlike the plant pathogen *Fusarium sambucinum* which displays variation in this region.

Example 2

Detection of DNA from *Candida albicans* Cells in Blood by Use of the Polymerase Chain Reaction (POR) Growth of *C. albicans*

*C. albicans* strain 36B was grown on Sabouraud's dextrose agar Emmons slants for 48 h at 25° C. Cells were harvested by washing each slant with 5 ml of 0.85% NaCl, centrifuged at 1500×g for 10 min, and resuspended to the appropriate concentration in freshly collected rabbit's blood or 0.85% saline.

Yeast cell lysis and DNA purification

Blood from adult female rabbits (New Zealand White, Myrtle's Rabbit Farm) was collected from the central ear artery into ISOLATOR 10 ® microbial tubes (Wampole Laboratories, Cranbury, N.J.) containing an aqueous solution of 1 unit of purified saponin, 8 ml/L polypropylene glycol, 9,6 g/L Na polyanetholesulfonate and 16 g/L $(Na)_2EDTA$; EDTA-coated tubes (Becton Dickinson, Rutherford, N.J.); or heparinized tubes (Becton Dickinson). *C. albicans* strain 36B (Quebec Gynecological Institute, Montreal, Quebec) cells were then introduced and samples were centrifuged at 3000×g for 30 min. Supernatants were removed and an equal volume of deionized water was added to lyse residual blood cells. Remaining *C. albicans* cells were washed in 0.85% NaCl and pelleted by centrifugation at 1500×g for 10 min. ISOLATOR 10 ® tubes have proven superior to other blood collection systems for the recovery of viable *C. albicans* cells from blood (Jones, 1990). The use of the ISOLATOR 10 ® tubes for blood collection resulted in PCR amplification of candidal DNA whereas the use of EDTA- or heparin-coated tubes did not.

*C. albicans* DNA was extracted and purified using the ISOQUICK ® nucleic acid extraction kit according to the manufacturer's instructions with the addition of ZYMOLASE ®-100T, to allow its use with fungi, since the ISOQUICK ® kit was developed by MicroProbe Corporation for the isolation and purification of DNA from only mammalian cells and gram negative bacteria. Briefly, pelleted cells were suspended in 100 μl of sample buffer for 15 min after which 100 μl of lysis buffer was added. The mixture was incubated at 25° C. for 1 h. Selected samples contained ZYMOLYASE (ZYMOLYASE ®-100T, Seikagaku Corp., Tokyo, Japan; 5 mg/ml in 1.0M sorbitol, 0.1M trisodium citrate, and 0.1% 2-mercaptoethanol) during the lysis step and were rocked at 16 cycles per min to optimize breakage of *C. albicans* cells. The addition of ZYMOLYASE ®-100T to the lysis step allowed for successful adaptation of the ISOQUICK ® kit for use with *C. albicans* cells. Alternatively, *C. albicans* cells were disrupted using a mini bead beater (Biospec Products, Bartlesville, Okla.) (Glee et al. 1987). Cells (1 ml) were delivered into Sarstedt microfuge tubes containing 1 ml of 0.5 mm diameter glass beads and beaten at maximum speed for 2 min. A third method released *C. albicans* DNA by boiling $1×10^7$ cells per ml in 2 mls of deionized water in an Eppendorf microcentrifuge tube for 30 min. Mechanical disruption of *C. albicans* cells by bead beating or boiling was less effective in producing PCR amplifiable DNA; these methods may be too harsh, resulting in shearing or fragmentation of DNA. For precipitation of the DNA sodium acetate and other components of the ISOQUICK ® kit were used as directed.

After lysis, DNA was purified with the extraction matrix provided in the ISOQUICK ® kit, precipitated with sodium acetate in the presence of isopropanol, and the precipitated DNA was dried by vacuum centrifugation for 15 min.

PCR amplification of genomic DNA

Universal fungal primer pairs, ITS1 and 2 or ITS3 and 4, synthesized by the CDC core facility., and the GeneAmpR DNA amplification reagent kit using native Taq DNA polymerase (250 U, Perkin Elmer Cetus, Alameda, Calif.) were used for PCR amplification of genomic DNA (Saiki et al. 1988). These primers amplify DNA from all fungi and some parasites. Examples of the ITS1, ITS2, ITS3 and ITS4 primers are shown in the Sequence Listing as SEQ ID NOs:1, 4, 2 and 3, respectively. The reaction consisted of the following: 53.5 $\mu$l of double distilled, sterile water, 10 $\mu$l of 10×reaction buffer, 16 $\mu$l of a mixture of equimolar (1.25 mM) quantities of dATP, dCTP, dGTP, and dTTP, 5 $\mu$l of 20 $\mu$M ITS1 or 3, 5 $\mu$l 20 $\mu$M ITS2 or 4, 10 $\mu$l of target DNA, 0.5 $\mu$l of Taq polymerase, and 6 $\mu$l of 25 mM $MgCl_2$. Samples were overlaid with mineral oil prior to placement in the thermal cycler (Perkin Elmer Cetus) to minimize evaporation during DNA amplification. Samples were initially denatured in the thermal cycler at 95° C. for 5 min. This was followed by 30 cycles of: denaturation at 95° C. for 1 min, annealing at 50° C. for 2 min, and extension at 72° C. for 1.5 min. Final extension occurred at 72° C. for 5 min.

After amplification, mineral oil was discarded. An equal volume of chloroform was added to the samples which were then centrifuged for 5 min at 4100×g to extract residual mineral oil. The aqueous layer was removed and the DNA precipitated from it by adding 2 volumes of ice-cold 100% ethanol followed by incubation for 30 min at −70° C. Samples were then centrifuged for 1 min at 4100×g, the ethanol removed, the samples dried under vacuum, and resuspended in 20 $\mu$l of TE buffer (20 mM Tris plus 1 mM EDTA, pH 8.0). Amplified DNA was visualized after agarose (1% agarose plus 1% Nu-Sieve in TE buffer) gel electrophoresis by ethidium bromide staining or by dot blot hybridization analysis.

Dot blot hybridization

C. albicans strain 3307 DNA was used as a probe for the dot blot. To make the probe, 20 ng of C. albicans 3307 genomic DNA was PCR-amplified using ITS1 and ITS2 or ITS3 and ITS4 as primer pairs. The PCR product was then electrophoresed on an agarose gel and the resultant DNA band cut out of the gel. The product was extracted from the gel by the freeze-squeeze method of Thuring et al (Thuring et al., 1975). The DNA probe was labeled by incubating overnight with digoxigenin-dUTP from a nonradioactive-DNA labeling and detection kit according to the manufacturers instructions ("Genius" kit, Boehringer Mannheim, Indianapolis, Ind.). Other genus or species specific probes derived from the nucleic acids of SEQ ID NOs:5-9 can also be used in this method.

Samples were prepared for the dot blot (Kafatos et al., 1979, Lasker et al., 1992) by diluting 10 $\mu$l of C. albicans DNA to 25 $\mu$l with TE buffer, adding NaOH to a final concentration of 0.3M, and incubating for 10 min at 25° C. An equal volume of 2.0M ammonium acetate was then added to each sample on ice. Each sample was then dotted under vacuum onto a nitrocellulose filter using a dot blot apparatus (BioRad, Richmond, Calif.) according to the manufacturer's instructions. The filter was then removed from the apparatus and dried at 80° C. under vacuum for 2 h. The dried filter was placed in a plastic bag, sealed, and prehybridized with single-stranded salmon sperm DNA (10 $\mu$g/ml) overnight in a 65° C. water bath.

The digoxigenin-labeled probe was denatured by boiling for 5 min, added to the filter in the plastic bag, and placed in a 65° C. water bath overnight. The filter was then washed twice for 30 min each in citrated saline (0.3M NaCl with 0.03 M sodium citrate, pH 7.0) and 0.1% SDS at 60° C. (Lasker et al., 1992). Washed filters were incubated for 30 min at 25° C. with an anti-digoxigenin antibody (1:5000) labeled with alkaline phosphatase. Chromogen (nitroblue tetrazolium salt and 5-bromo-4-chloro-3-indolyl phosphate) was added (Lasker et al., 1992) and color developed for 6 h at 25° C. in the dark.

"Booster" PCR amplification

"Booster" PCR amplification was performed by the method of Ruano et al. (Ruano et al., 1989). Briefly, the same protocol as outlined above was used, but after 15 cycles of PCR amplification, samples were removed from the thermal cycler and fresh primers were added to a final concentration of 40 $\mu$M. The samples were then returned to the thermal cycler for 15 additional cycles and final extension. The level of sensitivity of detection of the PCR product from cells introduced into blood was improved from $10^5$ cells per ml to $10^3$ cells per ml as detected by ethidium bromide stained agarose gels. However, the specificity of this system was poor since the negative control became positive.

Detection of PCR amplified products from C. albicans in saline by agarose gel electrophoresis A comparison of C. albicans DNA isolated and purified from saline using the ISOQUICK ® kit alone to that obtained by the use of ZYMOLYASE ®-100T plus the kit was performed. C. albicans cells ($10^7$/ml saline) were lysed at either 37° C. or 25° C. The combined use of ZYMOLYASE and the ISOQUICK ® kit (at either 25° C. or 37° C.) resulted in enhanced recovery of purified DNA relative to the kit alone.

To determine the sensitivity of the ZYMOLYASE ®-100T plus ISOQUICK ® method for cell breakage and DNA purification, C. albicans cells were then serially diluted in saline ($10^7$ to $10^1$ cells per ml) before breakage. Ethidium bromide stained agarose gels demonstrated that $10^3$ cells per ml could be detected by this method. Based on these results, all subsequent experiments used ZYMOLYASE ®-100T followed by DNA purification with the ISOQUICK ® kit at 25° C.

Detection of PCR amplified products of C. albicans in blood by agarose gel electrophoresis To determine if the ZYMOLYASE ®-100T plus ISOQUICK ® kit method could be used to detect C. albicans in blood, $10^7$ C. albicans cells per ml was introduced into freshly collected rabbit's blood as described above. Blood was collected into one of the following: ISOLATOR 10 ® microbial tubes, EDTA-coated tubes, or heparinized tubes. Amplified DNA was detected in the samples prepared from cells introduced into blood drawn into ISOLATOR 10 ® tubes only. No DNA was detected in samples where blood had been drawn into either only EDTA- or only heparin-coated tubes.

The sensitivity of detection for *C. albicans* DNA in blood using the ZYMOLYASE®-100T plus ISO-QUICK® kit method was determined by serially diluting *C. albicans* cells ($10^7$ to $10^1$ cells per ml) in blood drawn into ISOLATOR 10® tubes. Using agarose gel electrophoresis and ethidium bromide staining, $10^5$ cell per ml could be detected.

Dot blot hybridization for detection of PCR amplified products of *C. albican* in blood or saline.

In an effort to improve the sensitivity for detection of *C. albicans* DNA, a comparison was performed of the ethidium bromide-stained agarose gel method to a dot blot hybridization method for the detection of the PCR product. The dot blot method allowed detection of $10^1$ cells per ml in saline versus $10^3$ cells per ml detected by agarose gel electrophoresis and ethidium bromide staining. The sensitivity for detection of the PCR product of *C. albicans* cells introduced into blood was $10^1$ cells per ml by the dot blot method versus $10^5$ cells per ml for ethidium bromide stained agarose gels detection. The probe used for the above dot blot was *C. albicans*-specific. *C. tropicalis* DNA and human placental DNA did not react in the dot blot, supporting the specificity of the probe. Thus, the methods taught herein are capable of detecting Candida DNA in clinical samples such as blood.

Universal fungal primers as described herein provide the potential for amplification of DNA from all fungi. However, by using a *C. albicans*-specific DNA probe, as in the above-described dot blot hybridization step, the test was specific for *C. albicans*. The dot blot assay can be conducted using specific probes for other Candida species, as described herein, or other fungi. Furthermore, because the present method can gently extract DNA from clinical samples, the method can also use viral, bacterial or other fungal primers for the PCR reaction followed by specific DNA probes for each genus or species in the dot blot as described above.

Throughout this application various publications are referenced within parentheses. Full citations for these publications may be found at the end of the specification immediately preceding the Sequence Listing. The disclosures of these publications in their entireties are hereby incorporated by reference into this application in order to more fully describe the state of the art to which this invention pertains.

REFERENCES

Armstrong, C. 1989. Problems in Management of Opportunistic Fungal Diseases. *Rev. Infect. Dis.* 2:S1591–S1599.

Barns, S. M., Lane, D. J., Sogin M. L., Bibeau, C. and Weisburg, W. G. (1991) Evolutionary relationships among pathogenic Candida species and relatives. *J. Bacteriol.* 173:2250–2255.

Buchman, T. G., M. Rosser, W. G. Merz, and P. Charache. 1990. Detection of surgical pathogens by in vitro DNA amplification. Part I. Rapid identification of *Candida albicans* by in vitro amplification of a fungus-specific gene. *Surgery* 108:338–347.

Dams, E., Hendriks, L., Van de Peer, Y., Neefs, J. and Smits, G. (1988) Compilation of small ribosomal subunit RNA sequences. *Nucl. Acids Res.* 16:r87–r174.

Devereux, J., Haeberli, P. and Smithies, O. (1984) A comprehensive set of sequence analysis programs for the VAX. *Nucl. Acids Res.* 12:387–397.

Edman, J. C., Kovacs, J. A., Masur, H., Santi, D. V., Elwood, H. J. and Sogin, M. L. (1988) Ribosomal RNA shows Pneumocystis carinii to be a member of the fungi. *Nature* (London). 334:519–522.

Felsenstein, J. (1982) Numerical methods for inferring evolutionary trees. *Quart. Rev. Biol.* 57:379–404.

Felsenstein, J. (1985) Confidence limits on phylogenies: an approach using the bootstrap. *Evolution.* 39:783–791.

Glee, P. M., P. J. Russell, J. A. Welsch, J. C. Pratt, and J. E. Cutler. 1987. Methods of DNA extraction from *Candida albicans*. *Anal. Biochem.* 164:207–213.

Guthrie, C. and Fink, G. R. (1991) Guide to yeast genetics and molecular biology. *Meth. Enzol.* 194:3–20.

Jones, J. M. 1990. Laboratory diagnosis of invasive candidiasis. *Clin. Microbiol, Rev.* 3:32–45.

Kafatos, F. C., C. W. Jones, and A. Efstraliadis. 1979. Determination of nucleic acid sequence homologies and relative concentrations by a dot blot hybridization procedure. *Nucl, Acids Res.* 3:1541–1552.

Lasker, B. A., J. M. Brown, and M. M. McNeil. 1992. Identification and epidemiological typing of clinical and environmental isolates of the genus Rhodococcus with use of a digoxigenin-labeled rDNA gene probe. *Clin. Infect,. Dis.* 15:223–233.

Lasker, B. A., Carle, G. F., Kobayashi, G. S. and Medoff, G. (1989) Comparison of the separation of *candida albicans* chromosome-sized DNA by pulsed-field gel electrophoresis techniques. *Nucl. Acids Res,* 17:3783–3793.

Lehmann, P. F., Lin, D. and Lasker, B. A. (1992) Genotypic identification and characterization of species and strains within the genus Candida by using random amplified polymorphic DNA. *J. Clin. Micro* 30:3249–3254.

Magee, B. B., D'Souza, T. M. and Magee, P. T. (1987) Strain and species identification by restriction fragment length polymorphisms in the ribosomal DNA repeat of Candida species. *J. Bacteriol,* 169:1639–1643.

Messing, J., Crea, R. and Seeburg, P. H. (1981) A system for shotgun DNA sequencing. *Nucl. Acids Res,* 9:309–319.

Mitchell, T. G., White, T. J. and Taylor, J. W. (1992) Comparison of 5.8S ribosomal DNA sequences among the basidiomycetous yeast genera Cystofilobasidium, Filobasidium and Filobasdiella. *J. Med. Vet. Mycol.* 30:207–218.

Miyakawa, y., T. Mabuchi, K. Kagaya, and Y. Fukagawa. 1992. Isolation and detection of *Candida albicans* by polymerase chain reaction. *J. Clin. Micro.* 30:894–900.

Needleman, S. B. and Wunsch, C. D. (1970) A general method applicable to the search for similarities in the amino acid sequence of two proteins. *J. Mol. Biol.* 48:443–453.

Odds, F. C. 1988. Candida and Candidosis: A Review and Bibliography, 2nd Ed., Philadelphia: Bailere Tindall.

O'Donnell, K. (1992) Ribosomal DNA internal transcribed spacers are highly divergent in the phytopathogenic ascomycete Fusarium sambucinum (Gibberella pulicaris). *Curr. Genet.* 22:213–220.

Ruano, G. W., W. Tenton, and K. K. Kidd. 1989. Biphasic amplification of very dilute DNA samples via "booster" PCR. *Nucl. Acids Res.* 3:5407–5411.

Saiki, K. K., D. H. Gelfand, S. Stafford, S. J. Scharf, R. Higuchi, G. F. Horn, K. B. Mullis, and H. A. Erlich. 1988. Primer directed enzymatic ampl;ification od DNA with thermostable DNA polymerase. *science* 239:487–491.

Sambrook, J., Fritsch, E. F. and Maniatis, T. Molecular Cloning: A laboratory manual. Cold Spring Harbor Laboratory Press. Cold Spring Harbor, N.Y. 1989.

Sanger, F., Nicklen, S. and Coulson, A. R. (1977) DNA sequencing with chain-terminating inhibitors. *Proc. Natl. Acad. Sci. USA.* 74:5463–5467.

Smith, L. M., Sanders, J. Z., Kaiser, R. J., Hughes, P., Dodd, C., Connell, C. R., Heiner, C., Kent, S. B. H. and Hood, L. E. (1986) Fluorescence detection in automated DNA sequence analysis. *Nature* (London). 321:674–679.

Telenti, A., G. R. Roberts. 1989. Fungal blood cultures. *Eur. J. Clin. Microbiol. Infect. Dis.* 8:151–156.

Thrash-Bingham, C., and Gorman, J. A. (1992) DNA translocations contribute to chromosome-length polymorphisms in *Candida albicans. Curr. Genet.* 22:93–100.

Thuring, R. W. J., J. P. Sanders, and P. Borst. 1975. A freeze squeeze method for recovering long DNA from agarose gels. *Anal, Biochem.* 66:213–220.

Van der Walt, J. P. and Yarrow, D. (1984) Methods for the Isolation, maintenance, classification and identification of yeasts. in Kreger-van Rij, N. J. W. (Ed). The yeasts: A taxonomic study. Elsevier, Amsterdam. pp. 45–104.

White, T. J., Bruns, T. D., Lee S. B. and Taylor, J. W. (1990) Amplification and direct sequencing of fungal ribosomal RNA genes for phylogenetics. in Innis, M. A., Gelfand, D. H., Sninsky, J. J. and White, T. J. (Eds). PCR Protocols. A guide to methods and applications. Academic Press, San Diego. pp.315–322.

---

What is claimed is:

1. An isolated double-stranded nucleic acid consisting of the nucleotide sequence defied in the Sequence Listing by SEQ ID NO:5.

2. An isolated nucleic acid that specifically hybridizes with the nucleic acid of claim 1.

3. A method of diagnosing systemic candidiasis in a subject comprising the steps of:
   a. collecting blood from the subject into tubes containing detergent, polypropylene glycol, sodium polyanetholesulfonate, and sodium ethylene diamine tetraacetic acid;
   b. lysing Candida cells using ZYMOLYASE®-100T agitation;
   c. extracting and precipitating the DNA from the lysed cells;
   d. amplifying the precipitated DNA using universal fungal primer pairs that amplify the internal transcribed spacer regions of the Candida ribosomal DNA; and
   e. detecting amplified DNA from as few as 1 Candida cell per 100 microliters of blood by hybridizing the amplified DNA with a probe that specifically hybridizes with Candida DNNA, the presence of hybridization indicating systemic candidiasis.

4. The method of claim 3, wherein the lysis step further uses the lysis buffer from the ISOQUICK® kit.

5. The method of claim 3, wherein the agitation is by rocking at 16 cycles per minute.

6. The method of claim 3, wherein the extracting step uses the extraction matrix in the ISOQUICK® kit.

7. The method of claim 3, wherein one of the primers of the primer pair is derived from the internal transcribed spacer 1 and the other primer of the primer pair is derived from the internal transcribed spacer 2.

8. The method of claim 3, wherein one of the primers of the primer pair is derived from the internal transcribed spacer 3 and the other primer of the primer pair is derived from the internal transcribed spacer 4.

9. The method of claim 3, wherein the detecting step hybridization is by dot blot hybridization.

10. The method of claim 3, wherein the DNA that is amplified is from *Candida albicans* and wherein the probe specifically hybridizes with the nucleic acid of claim 1.

* * * * *

UNITED STATES PATENT AND TRADEMARK OFFICE
CERTIFICATE OF CORRECTION

PATENT NO. : 5,426,027
DATED : June 20, 1995
INVENTOR(S) : Timothy J. Lott, et al It is certified that error appears in the above-indentified patent and that said Letters Patent is hereby corrected as shown below:

In column 17, line 34, delete "defied" and insert therefor --defined--. In column 18, line 32 delete "DNNA" and insert therefor --DNA--.

Signed and Sealed this

Nineteenth Day of December, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,426,027
DATED : June 20, 1995
INVENTOR(S) : Timothy J. Lott et al.

Page 1 of 1

It is certified that error appears in the above-identified patent and that said Letters Patent is hereby corrected as shown below:

Column 17,
Line 34, delete "defied" and insert therefor -- defined --.

Column 18,
Line 32, delete "DNNA" and insert therefor -- DNA --.

Signed and Sealed this

Twenty-sixth Day of March, 2002

Attest:

JAMES E. ROGAN
Attesting Officer
Director of the United States Patent and Trademark Office

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

TCCGTAGGTG AACCTGCGG        19

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GCATCGATGA AGAACGCAGC        20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

TCCTCCGCTT ATTGATATGC        20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GCTGCGTTCT TCATCGATGC 20

( 2 ) INFORMATION FOR SEQ ID NO:5:

( i ) SEQUENCE CHARACTERISTICS:
        ( A ) LENGTH: 151 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:5:

CTCCCTCAAA CCGCTGGGTT TGGTGTTGAG CAATACGACT TGGGTTTGCT TGAAAGACGG 60

TAGTGGTAAG GCGGGATCGC TTTGACAATG GCTTAGGTCT AACCAAAAAC ATTGCTTGCG 120

GCGGTAACGT CCACCACGTA TATCTTCAAA C 151

( 2 ) INFORMATION FOR SEQ ID NO:6:

( i ) SEQUENCE CHARACTERISTICS:
        ( A ) LENGTH: 124 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:6:

CTCCCTCAAA CCCTCGGGTT TGGTGTTGAG CGATACGCTG GGTTTGCTTG AAAGAAAGGC 60

GGAGTATAAA CTAATGGATA GGTTTTTTCC ACTCATTGGT ACAAACTCCA AAACTTCTTC 120

CAAA 124

( 2 ) INFORMATION FOR SEQ ID NO:7:

( i ) SEQUENCE CHARACTERISTICS:
        ( A ) LENGTH: 141 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:7:

CTCCCTCAAA CCCCCGGGTT TGGTGTTGAG CAATACGCTA GGTTTGTTTG AAAGAATTTA 60

ACCGTGGAAA CTTATTTTAA GCGACTTAGG TTTATCCAAA ACGCTTATTT TGCTAGTGGC 120

CACCACAATT TATTTCATAA C 141

( 2 ) INFORMATION FOR SEQ ID NO:8:

( i ) SEQUENCE CHARACTERISTICS:
        ( A ) LENGTH: 231 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:8:

CCTTCTCAAA CACATTGTGN TTGGTANTGA GTGATACNCN NTTTTGATNT AACTTNAAAT 60

TGTAGGCCAT ATCAGTATGT GGGACACGAG NGCAAGCTTC TCTATTAATC TGCTGCTGCT 120

TTGCGCGAGC GGCGGGGGTT AATACTCTAT TAGGTTTTAC CAACTCGGTG TTGATCTAGG 180

GAGGGATAAG TGAGTGTTTT GTGCGTGCTG GGCAGACAGA CGTCTTTAAG T 231

( 2 ) INFORMATION FOR SEQ ID NO:9:

( i ) SEQUENCE CHARACTERISTICS:
( A ) LENGTH: 177 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:9:

```
GAGCGTCGTT  TCCATCTTGC  GCGTGCGCAG  AGTTGGGTGA  GCGGANGTAC  CGACGTGTAA      60

AGAGCGTCGG  AGCTGCGACT  CNNCTGAAAG  GGAGCNNANT  GGCCCGAGCG  AACTAGACTT     120

TTTTTNAGGG  NCCGTTTTGG  GCCCCAGAAC  GNAGTTTTNC  CNAGGNCAAC  AAAAAGN       177
```

( 2 ) INFORMATION FOR SEQ ID NO:10:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:10:

```
GTAAAACGAC  GGCCAG                                                         16
```